United States Patent [19]

Salmon et al.

[11] Patent Number: 5,503,155
[45] Date of Patent: Apr. 2, 1996

[54] DRIVE CABLE HAVING INTERNAL LEAD WIRES

[75] Inventors: Stephen Salmon, Sunnyvale; Rizza Casasos, Newark; Veijo T. Suorsa, Fremont; David A. White, Sunnyvale, all of Calif.

[73] Assignee: CardioVascular Imaging Systems, Inc., Sunnyvale, Calif.

[21] Appl. No.: 188,165

[22] Filed: Jan. 26, 1994

[51] Int. Cl.⁶ ........................................ A61B 8/12
[52] U.S. Cl. .......................... 128/662.06; 128/662.03
[58] Field of Search .................. 128/660.09, 660.10, 128/662.03, 662.06

[56] References Cited

U.S. PATENT DOCUMENTS

| | | | |
|---|---|---|---|
| 4,466,443 | 8/1984 | Utsugi | 128/660.10 |
| 4,466,444 | 8/1984 | Baba | 128/660.10 |
| 4,794,931 | 1/1989 | Yock | 128/660 |
| 4,841,977 | 6/1989 | Griffith et al. | 128/660 |
| 4,951,677 | 8/1990 | Crowley et al. | 128/662 |
| 4,977,898 | 12/1990 | Schwarzschild et al. | 128/662.06 |
| 5,000,185 | 3/1991 | Yock | 128/662 |
| 5,002,059 | 3/1991 | Crowley et al. | 128/662 |
| 5,095,911 | 3/1992 | Pomeranz | 128/662 |
| 5,105,818 | 4/1992 | Christian et al. | 128/662.06 |
| 5,108,411 | 4/1992 | McKenzie | 606/159 |
| 5,115,814 | 5/1992 | Griffith et al. | 128/662.06 |
| 5,174,295 | 12/1992 | Christian et al. | 128/662.06 |
| 5,199,437 | 4/1993 | Langberg | 128/662 |
| 5,203,338 | 4/1993 | Jang | 128/662 |
| 5,209,235 | 5/1993 | Brisken et al. | 128/662 |
| 5,243,988 | 9/1993 | Sieben et al. | 128/662 |

FOREIGN PATENT DOCUMENTS

| | | |
|---|---|---|
| 9203095 | 3/1992 | WIPO . |
| 9316642 | 2/1993 | WIPO . |

OTHER PUBLICATIONS

Martin et al, Design Characteristics for Intravascular Ultrasonic Catheters, International Journal of Cardiac Imaging 4: 201–216, 1989.

*Primary Examiner*—George Manuel
*Attorney, Agent, or Firm*—Townsend and Townsend and Crew

[57] ABSTRACT

A flexible drive cable comprises a flexible cable body, a pair of electrically insulated wires disposed through an axial lumen of the cable body, and a resilient support tube disposed over the wire pair. The resilient support tube provides support for the wire pair to help the wire pair recover from bending and deformation which may occur during storage or use of the drive cable. The support tube is usually liquid impermeable to maintain an air gap around the wire pair. The air gap improves shielding and maintains a constant overall impedance across the drive cable. The drive cable may be combined with an ultrasonic transducer at its distal end to form an ultrasonic transmission core.

35 Claims, 1 Drawing Sheet

5,503,155

DRIVE CABLE HAVING INTERNAL LEAD WIRES

BACKGROUND OF THE INVENTION

1. Field of the Invention

The present invention relates generally to the construction of flexible, torque-transmitting elements, and more particularly to the construction of a drive cable for rotation of an ultrasonic transducer for use in vascular catheters.

Intravascular imaging of blood vessel lesions prior to percutaneous transluminal angioplasty, atherectomy, and other interventional procedures, promises to be of great benefit. A particularly successful design for an intravascular imaging apparatus employs a rotatable ultrasonic transducer, where the transducer is attached to the distal end of a flexible drive cable. The transducer may be rotated within a catheter body or a sheath in order to transmit an ultrasonic signal and produce a video image by well-known techniques.

Although very successful, the need to reduce the size of drive cable to very small diameters (to be compatible with introduction into very small coronary arteries) presents a number of technical challenges. In addition to the very small diameter, the drive cable should be highly flexible so that it can pass through tortuous regions of the vasculature, particularly the coronary arteries. It is also very important that the drive cable provides uniform rotation along its entire length, i.e. avoid rotational wind-up which can cause variations in the rotational speed of the transducer and resultant image distortion.

The construction of transducer drive cables for intravascular ultrasound devices is further complicated by the desire to run transducer lead wires through a lumen in the cable itself. Such designs avoid an increase in an effective diameter which would result from placing the leads on the surface of the drive cable. Coaxial lead cables have been utilized in the past and have the added advantage that they provide radiofrequency (RF) noise shielding. Coaxial cables, however, suffer in that they are generally large and difficult to use in the smallest intravascular devices, e.g. coronary devices.

Twisted pairs of insulated electrical wire have also been used as lead wires in the drive cables of ultrasonic imaging catheters. Such twisted pairs are advantageous since they are available in very small diameters, but problematic in that they can contribute to non-uniform torque-transmission properties of the drive cable. Such wires are typically formed from malleable metals, such as copper and silver, which can deform during storage and when the drive cable is bent during use. Such malleable metals are not highly resilient and do not tend to return to their initial, straightened condition, as is the case with the body of the flexible cable. Thus, deformed lead wires within the outer cable body can create slight bends and other non-uniformities within the entire drive cable assembly. If the drive cable is not perfectly straight, it cannot spin uniformly in a tortuous vessel and will preferentially favor certain configurations within the vessel as it is rotated. In some rotational positions, the drive cable will be in a relaxed state, while in other positions more resistance will be met due to the force required to straighten out the combined drive cable and internal lead wires. Such non-uniformities can result in non-uniform rotation of the drive shaft, which is disadvantageous for the reasons discussed above.

A second problem with twisted pairs of electrical lead wires within such drive cables results from their lack of shielding. The signals transmitted by such twisted pairs are subject to greater degradation than that experienced by signals traveling through a coaxial cable. Additionally, the dielectric constant surrounding the twisted wire pairs will change if a liquid comes in direct contact with the wires. Impedance matching of the ultrasonic transducer and twisted pair lead wires is typically accomplished in a dry environment. Many ultrasonic systems require that the drive cable be immersed in a flushing liquid in order to provide acoustic coupling for imaging. Should the flushing liquid penetrate the drive cable body, and thus contact the internal twisted pair of electrical leads, the impedance surrounding the leads can be greatly reduced. Such a reduction will interfere with the impedance match between the transducer/wire system and the display unit.

It would therefore be desirable to provide improved drive cables for ultrasonic transducers and other rotatable electrical sensors. It would be particularly desirable to provide drive cables which can be constructed to have very small diameters and employ a twisted pair of electrical lead wires, where the electrical lead wires do not substantially degrade the mechanical characteristics of the combination of cable and lead wires. Even more particularly, the combination of cable and lead wires should be able to provide for uniform torque-transmission along the entire length of the drive cable in order to produce ultrasonic images having minimum distortion. The drive cables should further provide enhanced RF shielding of the electrical leads and should further provide for sealing of the electrical leads so that the drive cable can be immersed in a flushing liquid without wetting the wire leads.

2. Description of the Background Art

Rotatable ultrasonic transmission core elements having internal signal leads are disclosed in U.S. Pat. Nos. 5,243,988; 5,203,338; 5,199,437; 5,002,059, 4,951,677; and 4,841,977; and WO 92/03095. Catheter guide wires having internal means for rotating an ultrasonic transducer are disclosed in U.S. Pat. No. 5,095,911 and WO 93/16642. Ultrasonic imaging catheters having internal drive cables which can carry signal leads are described in U.S. Pat. Nos. 5,000,185 and 4,794,931. U.S. Pat. No. 5,209,235 describes apparatus for coupling to lead wires from an ultrasonic imaging catheter. U.S. Pat. No. 5,108,411, describes a flexible catheter drive shaft made in part from counter wound helical coils.

SUMMARY OF THE INVENTION

According to the present invention, a flexible drive cable comprises a flexible cable body having a proximal end, a distal end, and an axial lumen therebetween, typically being in the form of a pair of counter-wound helical coils. A pair of elongate lead wires, typically formed from a malleable metal and in the form of a pair of twisted, insulated metal wires, is disposed in the lumen of the cable body. It has been found that by placing a resilient support tube over the wire pair, the tendency of the wires to deform the cable body and cause non-uniform rotation is greatly reduced. In particular, it has been found that thin-walled support tubes formed from polymeric materials, such as polyimides, provide resilient support for the malleable metal wires, allowing them to recover more fully from bending and deformation which may occur during storage and use. Moreover, by configuring the support tube as a cylinder, an air gap is formed at least partly around the wires to enhance impedance matching of the electrical wire leads with external system electronics. By providing a support tube which is impermeable to liquid penetration, wetting of the wire leads can be prevented (even when the catheter body is immersed in a flushing liquid or other fluid) and impedance matching of an ultrasonic transducer connected through the cable can be maintained. In a particular embodiment, the present invention is an imaging core comprising a drive cable as described above in combination with an ultrasonic transducer mounted at the distal end of the catheter body and connected to the pair of lead wires.

A further understanding of the nature and advantages of the invention will become apparent by reference to the remaining portions of the specification and drawings.

DETAILED DESCRIPTION OF SPECIFIC EMBODIMENTS

Figure 1:
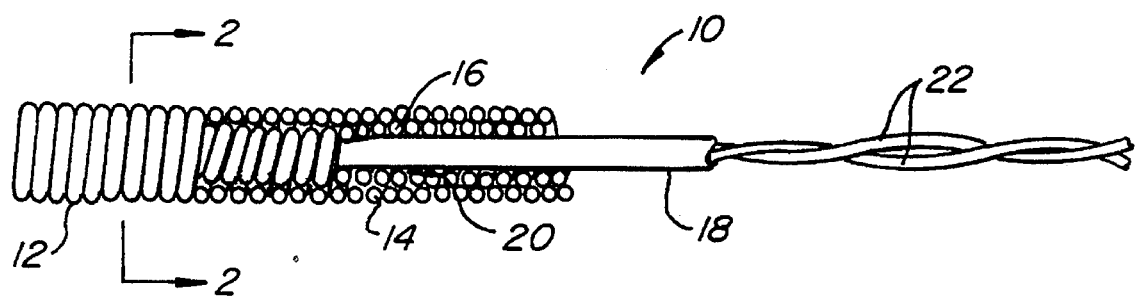
FIG. 1 is a detailed view of a drive cable constructed in accordance with the principles of the present invention shown with portions broken away.

The present invention comprises an improved cable and ultrasonic transmission core which may be used in a variety of medical devices for ultrasonic scanning and imaging. The cable and transmission core are particularly useful as drive cables in combination with vascular catheters and sheaths where an ultrasonic transducer attached to the cable is rotated within the catheter or sheath at a location of interest within a patient's vascular system. In such cases, the drive cable is rotated from its proximal end, typically using a motorized drive unit. The cables of the present invention may also find use in other applications where signal transmission leads are provided in article-structures, such as in ultrasonic Doppler catheters used for measuring blood flow.

The drive cable and ultrasonic transmission core are particularly suitable for use in small diameter catheters and sheaths which are intended for use in the coronary arteries, which are highly tortuous and can have very small diameters. Thus, the drive cables and imaging cores will find their greatest use with catheters having a size below 5 F (one French (F)=0.33 mm), preferably below 4 F, and often below 3 F, or smaller. The construction and use of vascular catheters and sheaths which could be adapted to employ the drive cables and imaging cores of the present invention are described in the following U.S. Pat. Nos. 5,243,988; 5,203,338; 5,095,911; 5,002,059; 5,000,185; 4,951,677; 4,841,977; and 4,794,931, the disclosures of which are incorporated herein by reference.

The drive cables of the present invention comprise a flexible cable body having a proximal end, a distal end, and an axial lumen extending from the proximal end to the distal end. The cable is preferably an elongate tubular or cylindrical member having a generally circular cross-section with sufficient torsional rigidity to transmit torque from the proximal end to the distal end. The length of the drive cable will be sufficient to extend from beyond the proximal end of an associated catheter or sheath to a location at or near the distal end of the catheter or sheath where the ultrasonic transducer or other electrical sensor will be located. For use with vascular catheters, the length of the drive cable body will usually be slightly more than that of the catheter, typically being in the range from about 10–250 cm, more usually being in the range from about 25–150 cm. The outer diameter of the cable body will be sufficiently small to fit within a central lumen of the associated catheter or sheath, typically being in the range from about 0.25 mm to 2 mm, preferably in the range from about 0.25 mm to 1 mm. For use with a preferred 2.9 F catheter sheath, the diameter of the drive cable will be about 0.75 mm.

The cable body will be flexible so that it may be introduced within a catheter or sheath through tortuous body passages, such as the coronary arteries, to a target location of interest. Since the regions of tortuosity encountered are usually closest to the target location, it is often necessary that only the distal-most portions of the catheter body be highly flexible. Thus, at least the distal 10 cm of the cable body will be highly flexible, preferably having a bending stiffness constant in the range from 0.015 to 0.15 in-lb-in, preferably from 0.025 to 0.050 in-lb-in. The bending stiffness constant is defined as $K_B$=RFd, where R=bending radius (inches); F=deflection force (lb.); and d=length of cable section (inches). The bending stiffness constant may be measured using a conventional three-point compression tester, such as the Instron Tensile Compression Tester. The cable section is placed on a pair of supports spaced-apart by a known length (L). A deflection force (F) is applied to the cable section at a location midway between the supports, and the resulting deflection is measured. The bending radius (R) can then be determined from the measured deflection. Alternatively, the radius can be determined by graphical analysis. In either case, the bending stiffness constant ($K_B$) can then be calculated using the above formula.

The flexibility of the proximal portion of the drive cable is less critical. Often, it will be simplest to fabricate the drive cable to have a constant flexibility over its entire length. In that case, the flexural stiffness of the bending constant of the entire drive cable will be within the above limits over its entire length. In other cases, however, it may be desirable to fabricate the drive cable in two or more sections, where each section has different mechanical properties. For example, in certain cases it would be desirable to construct the catheter body to have a more flexible distal portion and a less flexible proximal portion, where the more flexible distal portion has a bending constant within the above stated range while the proximal portion may be relatively less flexible, typically having a bending constant ($K_B$) within the range from 0.15 in-lb-in to 15 in-lb-in, typically from 3 in-lb-in to 7 in-lb-in. The more flexible distal portion of the cable body will thus have a length in the range from 10 cm to 250 cm, usually from 10 cm to 50 cm.

Conveniently, the drive cable body, or at least the more flexible distal portion thereof, will comprise a pair of nested, counter-wound helical coils, where the coils are each formed from metal wire, such as stainless steel. Suitable stainless steel is 304V stainless steel. The inner coil will have a diameter in the range from about 0.01 to 0.125 cm, usually from about 0.02 to 0.05 cm, while the outer coil will have a diameter in the range from about 0.015 to 0.15 cm, typically from about 0.03 to 0.1 cm. The wire diameter of the coils will usually be in the range from about 0.0005 to 0.02 cm, more usually being in the range from 0.005 to 0.01 cm. The coils will have a pitch which may vary from about 8 to 400 turns/cm, more usually being in the range from about 25 to 100 turns/cm. Usually, only two coils will be employed, but it would be possible to add additional coils so long as the overall diameter of the drive cable body is not increased beyond the desired range. The coils are wound in opposite directions so that when the cable body is rotated, one of the coils will tend to tighten, providing a very high torsional modulus of elasticity while reducing the flexural modulus of elasticity due to the flexible nature of the coil structures. Optionally, it may be desirable to cover the outer coil with an elastomeric sheath in order to enhance mechanical integrity of the coil and facilitate rotation of the cable body within a catheter lumen or sheath. Suitable elastomeric sheath materials include polyurethane, silicone, and the like.

In addition to counter-wound coils, other suitable catheter body constructions include braided metals, braided fibers, co-extruded polymers over braid structures, and the like. Any of these structures, as well as counter-wound coil structures, may also find use in a less flexible proximal portion of a catheter body. Additionally, thin-walled hypotube may be used as a less-flexible proximal portion of a drive cable body.

Electrical signal connection between the distal end and proximal end of the cable body will be provided by a pair of elongate, insulated metal core wires extending through the cable body lumen. The wires will be formed from a malleable material, typically electrically conductive metals, such as copper, silver, gold, aluminum, and various alloys thereof. The metal core wires will be covered by a conventional insulating material, such as an organic polymer, such as polyimide, polyurethane, polyester, nylon, and the like. Typically, the overall diameter of the wires (including insulation) will be in the range from 0.01 to 0.55 mm, usually from 0.05 to 0.15 mm. Suitable wires include 40 gauge electrical lead wire available from commercial suppliers, such as MWS Wire, Inc., Westlake Village, Calif.

The electrical lead wires will typically be in the form of a twisted pair, having from about 1 to 250 turns/cm, more usually from about 5 to 25 turns/cm. The maximum peripheral dimension of such twisted pairs will typically be twice that of the diameter of each individual wire including insulation, since the wires are disposed in a generally side-by-side configuration. While generally more useful, the electrical lead wires need not be in a twisted pair configuration, but instead can be oriented in an axially parallel manner, or could be irregularly wound over one another, without departing from the intent of the present invention.

The pair of electrical lead wires, as just described, will be disposed within an axial lumen of a resilient support tube, where the support tube helps the wire to recover from any bending and deformational stresses to which it may be subjected. In particular, the resilient support tube will tend to straighten out the wire pair after it has been wound for storage or after it has passed through tortuous regions of the blood vessel as part of introducing the associated device to a desired target location. Typically, the support tube will be relatively closely fitting over the outside of the wire pair, typically having an inside diameter in the range from 0.02 mm to 1.5 mm, more typically from 0.15 to 0.25 mm. Preferably, the support tube will be a thin-walled polymeric tube composed of an organic polymer selected from the group consisting of polyimide, polyurethane, polyethylene, polyester, nylon, and the like. The wall thickness of the tube will typically be in the range from 0.01 mm to 0.05 mm, preferably from 0.01 mm to 0.025 mm. The use of polyimide tubes is presently preferred, with suitable polyimide tubes having wall thicknesses of about 0.02 mm (0.0075 inch) being available from commercial suppliers, such as Micropolyx, Chattanooga, Tenn.

Construction of the flexible drive cable is relatively straight forward. The cable body may be fabricated using conventional techniques, generally as taught in U.S. Pat. No. 5,108,411, the disclosure of which has previously been incorporated herein by reference. Suitable insulated, metal core wires may also be obtained from commercial suppliers and may be twisted manually or using readily available twisting equipment. The twisted wire pair may then be drawn through a support tube having an inner diameter which is only slightly greater than the maximum peripheral dimension of the twisted wire pair. The combination of support tube and twisted wires may then be introduced through the central lumen of the cable body. Usually, the outer diameter of the support tube will be somewhat less than the inner diameter of the axial lumen within the cable body. The existence of clearance or a gap between the support tube in the inner surface of the cable body lumen is not problematic.

Once the drive cable of the present invention has been fabricated, it may be used as a part of a vascular catheter system, as described in U.S. Pat. Nos. 5,000,185 and 4,794,931, the disclosures of which have previously been incorporated herein by reference. Alternatively, it may be used to prepare an ultrasonic transmission core which in turn may be placed in an outer catheter or sheath body, as described in U.S. Pat. Nos. 5,243,988 and 5,203,338, the disclosures of which have previously been incorporated herein by reference.

Figure 2:
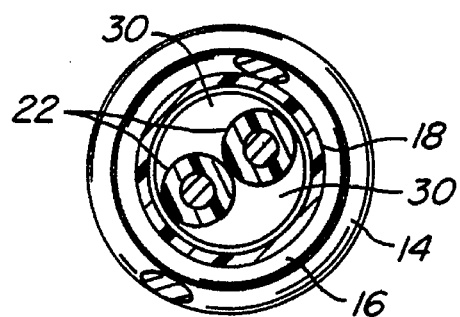
FIG. 2 is a cross-sectional view of the drive cable of FIG. 1 taken along line 2—2.

Turning now to FIGS. 1 and 2, an exemplary drive cable body 10 is illustrated. The drive cable body 10 includes a flexible, counter-wound coil 12 including an outer coil 14 and an inner coil 16. A support tube 18 is received within a central lumen 20 of the counter-wound coil 12, and a pair of twisted electrically insulated wires 22 are, in turn, received within a lumen of the support tube 18.

As best illustrated in FIG. 2, an air gap 30 is created on each side of the twisted wire pair 22. The air gaps 30 are in the form of a double helix which is complementary to the helical nature of wires 22. By providing a liquid-impermeable support tube 18, the air gap 30 will be maintained in a relatively dry condition, even when the drive cable 10 is immersed in a liquid, for example when the drive cable is being used within a fluid ultrasonic coupling medium. By maintaining the region about the wires 22 in a dry condition, particularly in the central region where the wires are in direct contact, the overall impedance match of the dry system will be maintained when the drive cable is immersed in a liquid, such as an ultrasonic flushing liquid.

Figure 3:
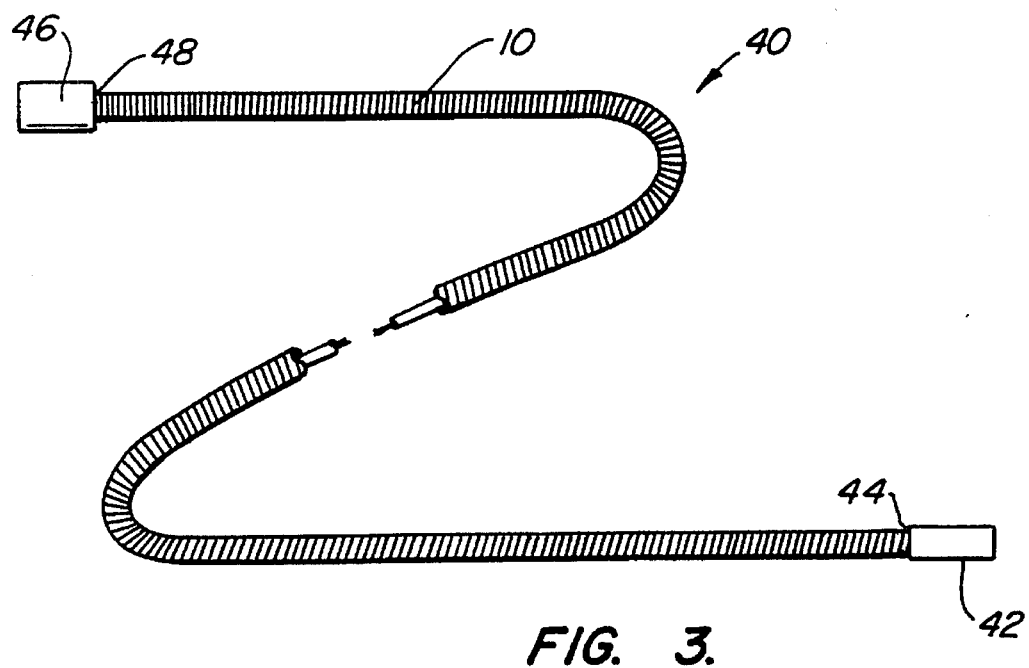
FIG. 3 illustrates the drive cable of FIGS. 1 and 2 shown with an ultrasonic transducer connected to its distal end and a connector housing connected to its proximal end.

Referring now to FIG. 3, the drive cable 10 may be incorporated in an ultrasonic transmission core 40 by securing an ultrasonic transducer 42 at its distal end 44 and a coupling element 46 at its proximal end 48. The transducer element 44 may optionally include a mirror in tandem to direct the scanning ultrasonic signal radially outward. Alternatively, the ultrasonic transducer itself may be directed generally radially outward in order to effect scanning as the drive cable body 10 is rotated.

Although the foregoing invention has been described in some detail by way of illustration and example, for purposes of clarity of understanding, it will be obvious that certain changes and modifications may be practiced within the scope of the appended claims.

What is claimed is:

1. An improved ultrasonic transmission core of the type including a flexible cable body, a pair of elongate, malleable wires disposed in a lumen of the cable body, and an ultrasonic transducer mounted on a distal end of the cable body and attached to the wire pair, wherein the improvement comprises a resilient polymeric support tube disposed closely over the wire pair and closely within the axial lumen of the flexible cable body, the support tube extending substantially the entire length of the cable body.

2. An improved ultrasonic transmission core as in claim 1, wherein the wires are in a twisted pair.

3. An improved ultrasonic transmission core as in claim 2, wherein the wires are helically twisted with a pitch in the range from 1 turns/cm to 250 turns/cm.

4. A improved ultrasonic transmission core as in claim 2, wherein the support tube is generally cylindrical and fits closely over the wires so that a pair of air-filled helical voids is formed.

5. An improved ultrasonic transmission core as in claim 4, wherein the support tube is impermeable to liquids, whereby the interior of the support tube will remain dry when the drive cable is immersed in a liquid.

6. An improved ultrasonic transmission core as in claim 1, wherein at least a distal portion of the cable body has a bending stiffness constant below about 0.15 in-lb-in.

7. An improved ultrasonic transmission core as in claim 6, wherein the flexible cable body comprises a pair of counter-wound helical coils.

8. An improved ultrasonic transmission core as in claim 6, wherein the insulated wires have a diameter in the range from 0.01 mm to 0.55 mm.

9. An improved ultrasonic transmission core as in claim 1, wherein the resilient support tube is composed of a material selected from the group consisting of polyimide, polyurethane, polyethylene, polyester, and nylon.

10. An improved ultrasonic transmission core as in claim 9, wherein the polymeric tube has an inside diameter in the range from 0.02 mm to 1.5 mm and a wall thickness in the range from 0.01 mm to 0.05 mm.

11. An improved ultrasonic transmission core of the type including a flexible cable body, a pair of elongate, malleable wires disposed in a lumen of the cable body, and an ultrasonic transducer mounted on a distal end of the cable body and attached to the wire pair, wherein the improvement comprises a resilient polymeric support tube disposed closely over the wire pair and closely within the axial lumen of the flexible cable body wherein the wires are a helically twisted pair with a pitch in the range from 1 turn/cm to 250 turns/cm.

12. A improved ultrasonic transmission core as in claim 11, wherein the support tube is generally cylindrical and fits closely over the wires so that a pair of air-filled helical voids is formed.

13. An improved ultrasonic transmission core as in claim 12, wherein the support tube is impermeable to liquids, whereby the interior of the support tube will remain dry when the drive cable is immersed in a liquid.

14. An improved ultrasonic transmission core as in claim 11, wherein at least a distal portion of the cable body has a bending stiffness constant below about 0.15 in-lb-in.

15. An improved ultrasonic transmission core as in claim 14, wherein the flexible cable body comprises a pair of counter-wound helical coils.

16. An improved ultrasonic transmission core as in claim 14, wherein the insulated wires have a diameter in the range from 0.01 mm to 0.55 mm.

17. An improved ultrasonic transmission core as in claim 11, wherein the resilient support tube is composed of a material selected from the group consisting of polyimide, polyurethane, polyethylene, polyester, and nylon.

18. An improved ultrasonic transmission core as in claim 17, wherein the polymeric tube has an inside diameter in the range from 0.02 mm to 1.5 mm and a wall thickness in the range from 0.01 mm to 0.05 mm.

19. An improved ultrasonic transmission core of the type including a flexible cable body, a pair of elongate, malleable wires disposed in a lumen of the cable body, said cable body having a bending stiffness constant below about 0.15 in-lb-in, and an ultrasonic transducer mounted on a distal end of the cable body and attached to the wire pair, wherein the improvement comprises a resilient polymeric support tube disposed closely over the wire pair and closely within the axial lumen of the flexible cable body.

20. An improved ultrasonic transmission core as in claim 19, wherein the wires are in a twisted pair.

21. An improved ultrasonic transmission core as in claim 20, wherein the wires are helically twisted with a pitch in the range from 1 turn/cm to 250 turns/cm.

22. A improved ultrasonic transmission core as in claim 20, wherein the support tube is generally cylindrical and fits closely over the wires so that a pair of air-filled helical voids is formed.

23. An improved ultrasonic transmission core as in claim 22, wherein the support tube is impermeable to liquids, whereby the interior of the support tube will remain dry when the drive cable is immersed in a liquid.

24. An improved ultrasonic transmission core as in claim 19, wherein the flexible cable body comprises a pair of counter-wound helical coils.

25. An improved ultrasonic transmission core as in claim 24, wherein the insulated wires have a diameter in the range from 0.01 mm to 0.55 mm.

26. An improved ultrasonic transmission core as in claim 24, wherein the resilient support tube is composed of a material selected from the group consisting of polyimide, polyurethane, polyethylene, polyester, and nylon.

27. An improved ultrasonic transmission core as in claim 26, wherein the polymeric tube has an inside diameter in the range from 0.02 mm to 1.5 mm and a wall thickness in the range from 0.01 mm to 0.05 mm.

28. An improved ultrasonic transmission core of the type including a flexible cable body, a pair of elongate, malleable wires disposed in a lumen of the cable body, and an ultrasonic transducer mounted on a distal end of the cable body and attached to the wire pair, wherein the improvement comprises a resilient polymeric support tube disposed closely over the wire pair and closely within the axial lumen of the flexible cable body, wherein the resilient support tube is composed of a material selected from the group consisting of polyimide, polyurethane, polyethylene, polyester, and nylon, and wherein the polymeric tube has an inside diameter in the range from 0.02 mm to 1.5 mm and a wall thickness in the range from 0.01 mm to 0.05 mm.

29. An improved ultrasonic transmission core as in claim 28, wherein the wires are in a twisted pair.

30. An improved ultrasonic transmission core as in claim 29, wherein the wires are helically twisted with a pitch in the range from 1 turn/cm to 250 turns/cm.

31. A improved ultrasonic transmission core as in claim 29, wherein the support tube is generally cylindrical and fits closely over the wires so that a pair of air-filled helical voids is formed.

32. An improved ultrasonic transmission core as in claim 31, wherein the support tube is impermeable to liquids, whereby the interior of the support tube will remain dry when the drive cable is immersed in a liquid.

33. An improved ultrasonic transmission core as in claim 28, wherein at least a distal portion of the cable body has a bending stiffness constant below about 0.15 in-lb-in.

34. An improved ultrasonic transmission core as in claim 33, wherein the flexible cable body comprises a pair of counter-wound helical coils.

35. An improved ultrasonic transmission core as in claim 33, wherein the insulated wires have a diameter in the range from 0.01 mm to 0.55 mm.

* * * * *